Sept. 22, 1970 F. T. ELLIOTT, JR Plant Pat. 2,990
PEACH TREE
Filed July 22, 1968
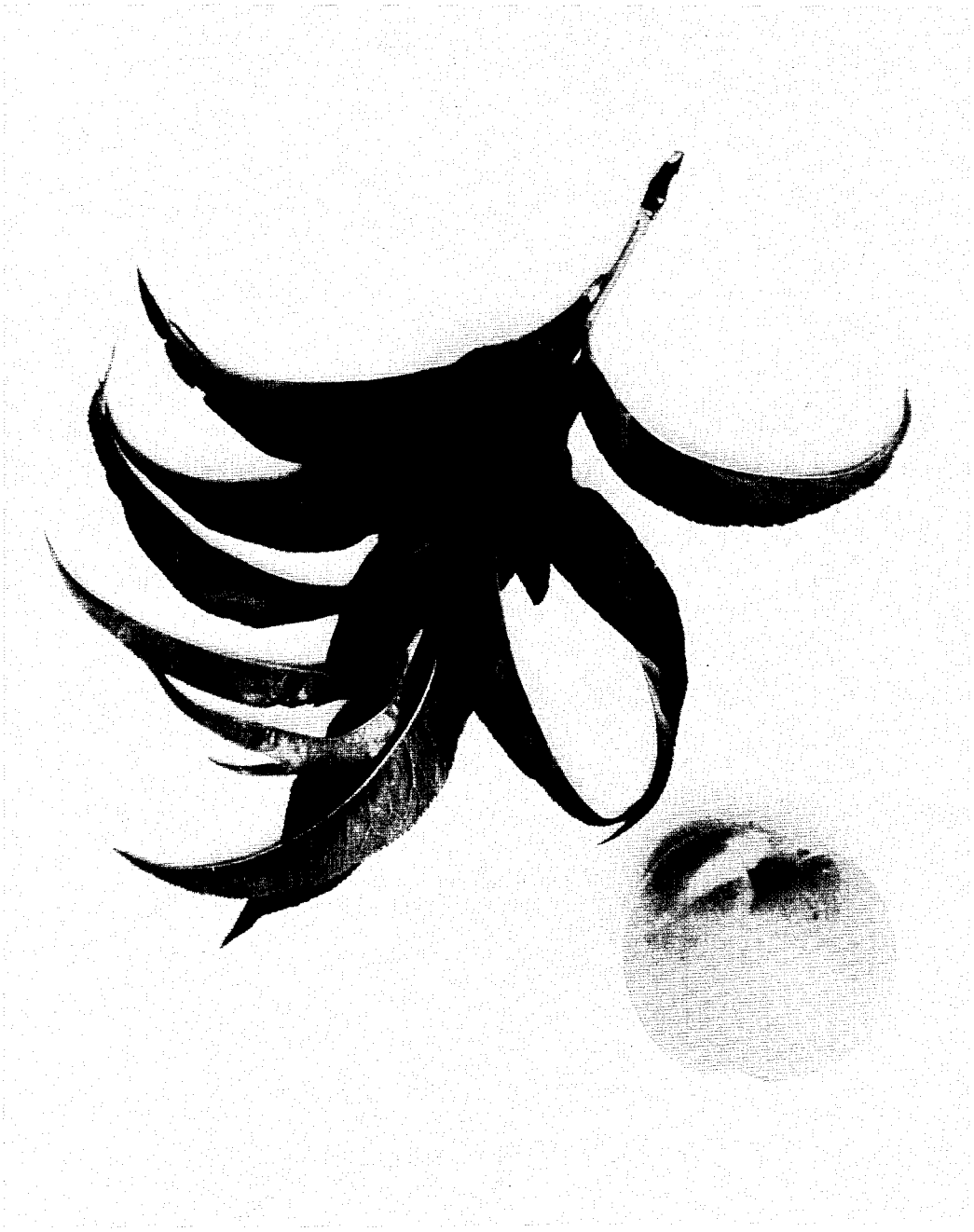
INVENTOR
Frank T. Elliott Jr.
BY
Webster & Webster
ATTORNEYS United States Patent Office Plant Pat. 2,990
Patented Sept. 22, 1970

2,990
PEACH TREE

Frank T. Elliott, Jr., Visalia, Calif., assignor to Reedley Nursery, Inc., Reedley, Calif., a corporation of California Filed July 22, 1968, Ser. No. 746,728
Int. Cl. A01h 5/03
U.S. Cl. Plt.—43 1 Claim

ABSTRACT OF THE DISCLOSURE

A variety of peach tree, of medium size and vigorous, spreading and open in growth, which is a regular and productive bearer of large to medium size semifree to clingstone fruit having yellow flesh, and yellow skin substantially overspread with red at maturity.

*Origin of the variety*

The variety of peach tree herein disclosed was discovered by me growing as a bud mutation on a mature Royal May (U.S. Plant Pat. No. 1,516) peach tree in an orchard ranch, of which I am one of the owners, located near Arvin, Kern County, California; the discovery having been made by reason of the fact that the fruit on the mutation limb colored and ripened earlier—and hence was drawn to my attention—than the fruit on the remainder of the tree.

*Asexual reproduction of the variety*

Subsequent to discovery of the present variety, and recognizing its potential commercial value, it was asexually reproduced, under my direction, by budding on mature nectarine trees in the orchard hereinbefore mentioned. Such reproductions, when they bore fruit, were carefully compared with the parent mutation and were found to carry forward all of the characteristics thereof.

*Summary of the variety*

The present variety of peach tree is of medium size, vigorous, spreading and open in growth, and a regular and productive bearer of large to medium size semifree to clingstone fruit, having yellow flesh, and yellow skin substantially overspread with red at maturity; the variety in tree and fruit being, in general, quite similar to the Royal May, but distinctively characterized, in comparison, by an earlier ripening period. More particularly, the fruit of the present variety ripens, under like soil and climatic conditions, about three to five days earlier than the Royal May and approximately with the Mayflower (unpatented).

The present variety of peach tree is—under like soil and climatic conditions—further distinctively characterized, in comparison to the Royal May, by fruit which—at maturity—is slightly smaller in size, somewhat firmer of flesh with slightly less soluble solids, and not quite as free at the pit.

*Brief description of the drawing*

The drawing is an illustration, by photographic reproduction in color, of a twig with leaves, and a whole fruit.

*Description of the variety*

The botanical details of this new and distinct variety of peach tree—with color definitions (except those in common color terms) referenced to Maerz and Paul Dictionary of Color—are as follows:

Tree:
- *Size.*—Medium.
- *Vigor.*—Vigorous.
- *Growth.*—Spreading.

- *Density.*—Open.
- *Production.*—Productive.
- *Bearing.*—Regular bearer.

Trunk:
- *Size.*—Medium.
- *Texture.*—Smooth.

Branches:
- *Size.*—Medium.
- *Texture.*—Smooth.

Leaves:
- *Size.*—Large: Average length (mature)—6½." Average width (mature)—1⅜".
- *Form.*—Lanceolate.—Acutely pointed.
- *Thickness.*—Medium.
- *Margin.*—Crenate.
- *Petiole.*—Medium length, medium thickness.
- *Glands.*—Average number—3, Reniform. Positioned usually 2 on petiole and 1 or more on blade.
- *Color.*—Top Side—Medium green (23–J–9), Under Side—Lighter green (22–K–8).

Flower Buds:
- *Size.*—Medium.
- *Form.*—Conic.

Flowers:
- *Blooming Period.*—About with the July Elberta (U.S. Plant Pat. No. 15). Early to medium, as compared with other varieties.
- *Size.*—Medium.

Fruit:
- *Maturity when described.*—Hard ripe—May 17, 1968.
- *Date of first picking.*—May 15, 1968.
- *Date of last picking.*—May 25, 1968.
- *Size.*—Large to medium. Average diameter axially—2½". Average transversely in suture plane—2½".
- *Form.*—Uniform. Symmetrical. Globose.
- *Suture*—Shallow..
- *Ventral Surface.*—Rounded.
- *Lips.*—Equal.
- *Cavity.*—Rounded. Average depth—⅜". Average breadth—½".
- *Base.*—Oblique.
- *Apex.*—Short.
- *Pistil Point.*—Apical.

Skin:
- *Thickness.*—Medium.
- *Texture.*—Medium.
- *Tenacity.*—Tenacious to flesh.
- *Tendency To Crack.*—None in wet season.
- *Down.*—Scant. Short. Does not roll up when rubbed.
- *Color.*—Yellow (10–L–5 to 9–L–4) substantially overspread with bright red (5–L–5 to 6–L–6) at maturity; the red in part being streaked and mottled.

Flesh:
- *Juice.*—Moderate.
- *Texture.*—Firm. Meaty.
- *Fibers.*—Few.
- *Ripens.*—Evenly.
- *Flavor.*—Subacid.
- *Aroma.*—Wanting.
- *Eating Quality.*—Good.
- *Color.*—Yellow (9–J–4 to 10–J–5). Surface of pit cavity—yellow.

Stone:
- *Type.*—Semifree to cling.
- *Size.*—Medium. Average length—1⅛". Average breadth—1 1/16". Average thickness—¾".

*Form.*—Oblong.
*Base.*—Oblique.
*Hilum.*—Oblong.
*Apex.*—Rounded.
*Sides.*—Equal.
*Ridges.*—Rounded.
*Pits.*—Elongated.
*Ventral Edge.*—Thick.
*Dorsal Edge.*—Full, with shallow groove.
*Color of stone.*—Ecru (11–E–3).
*Color of kernal.*—Brown (14–I–11).

Use: Market.
Keeping quality: Good.
Shipping quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, which is of medium size, vigorous, spreading and open in growth, and a regular and productive bearer of large to medium size semi-free to clingstone fruit having yellow flesh, and yellow skin substantially overspread with red at maturity; the tree and its fruit being, in general, quite similar to the Royal May but distinctively characterized, in comparison, by a ripening period of about three to five days earlier and which is approximately with the Mayflower.

No references cited.

ROBERT E. BAGWILL, Primary Examiner